(12) United States Patent
Margreiter et al.

(10) Patent No.: US 6,555,518 B1
(45) Date of Patent: Apr. 29, 2003

(54) GEMCITABINE AS AN IMMUNOSUPPRESSIVE PHARMACEUTICAL AGENT

(75) Inventors: Raimund Margreiter, Reith b. Seefeld (AT); Günther Konwalinka, Innsbruck (AT)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/687,565

(22) Filed: Oct. 13, 2000

Related U.S. Application Data

(63) Continuation of application No. PCT/AT99/00093, filed on Apr. 14, 1999.

(30) Foreign Application Priority Data

Apr. 14, 1998 (AT) ................................................ 636/98

(51) Int. Cl.⁷ .............................................. A61K 31/00
(52) U.S. Cl. ........................... 514/2; 514/171; 514/183; 514/233.5; 514/262; 514/266; 514/274; 514/291
(58) Field of Search ................................ 514/262, 266, 514/274, 2, 171, 183, 233.5, 291; 544/276, 277, 314, 318, 153; 530/387.3; 540/460, 456

(56) References Cited

U.S. PATENT DOCUMENTS 4,808,614 A * 2/1989 Hertel .......................... 514/45
6,291,504 B1 * 9/2001 Nugiel ....................... 514/403

OTHER PUBLICATIONS

Physicians Desk Reference, no author listed, 2001.*

* cited by examiner

Primary Examiner—Mukund J. Shah
Assistant Examiner—Thomas McKenzie

(74) Attorney, Agent, or Firm—Elizabeth A. McGraw

(57) ABSTRACT

The present invention provides the use of a compound of the formula I

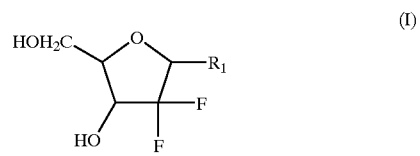

(I)

wherein:

$R_1$ is a base defined by one of the formulae

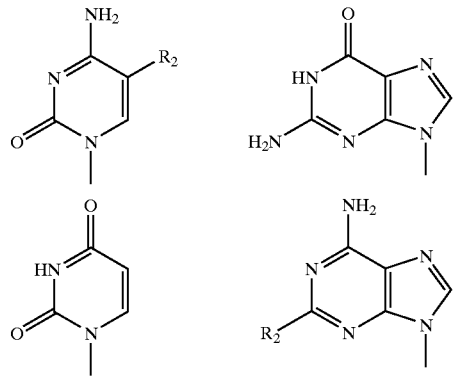

$R_2$ is hydrogen, $C_1$–$C_4$ alkyl, bromo, fluoro, chloro or iodo;

or a pharmaceutically-acceptable salt thereof for the manufacture of a medicament for immunosuppressive therapy of the human or animal body.

10 Claims, 1 Drawing Sheet

GEMCITABINE AS AN IMMUNOSUPPRESSIVE PHARMACEUTICAL AGENT

The present application claims priority under 35 U.S.C. §119 to Austrian Patent Application No. A 636/98, filed Apr. 14, 1998, the entire contents of which is incorporated herein by reference.

The present application is a continuation of international application PCT/AT99/00093, filed Apr. 14, 1999, designating the United.States, the entire contents of which is incorporated by reference.

BACKGROUND OF THE INVENTION

1. Field of the Invention

The present invention relates to the field of drug therapy and provides the new use of 2',2'-difluoronucleosides for the manufacture of compositions for immunosuppressive therapy and new pharmaceutical compositions and products for the treatment of the human and animal body.

2. State of the Art

The suppression of the reactivity of the immune system by immunosuppressive therapy is of major medical importance in the prevention of allograft rejection in transplant patients and in the treatment of autoimmune diseases. Over the past years a limited number of new drugs suitable for use in immunosuppressive therapy such as cyclosporin A, tacrolimus, mycophenolate mofetil, daclizumab and rapamycin have been developed.

There is still a vital need to develop more effective and tolerable methods of treating autoimmune diseases and of preventing allograft rejection in transplant patients. The present invention therefore seeks to provide new pharmaceutical compositions and products for use in this therapeutic area.

2'2'-difluoronucleosides have been shown to exhibit antiviral effects in vitro (U.S. Pat. No. 4,808,614) and oncolytic activity in standard cancer screens (U.S. Pat. No. 5,464,826). Among these compounds 2'-deoxy-2',2'-difluorocytidine (gemcitabine, dFdC) has been studied extensively with regard to its oncolytic activity. Kaye, *J. Clin. Oncol.* 12, 1527 (1994). Based on the results of these studies gemcitabine hydrochloride has received regulatory approval in more than 50 countries for treatment of non-small cell lung cancer and/or pancreatic cancer. Further studies for treatment of breast, bladder and ovarian cancer with gemcitabine are underway.

SUMMARY OF THE INVENTION

The present invention provides the use of a compound of the formula I

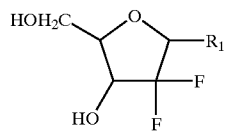

wherein:

$R_1$ is a base defined by one of the formulae

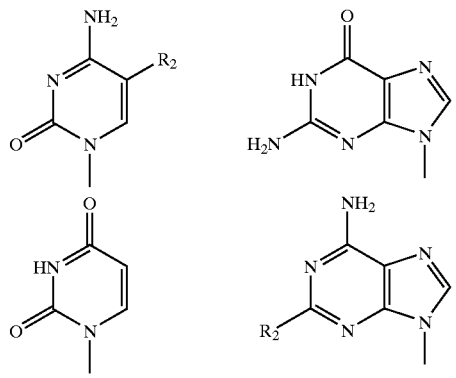

$R_2$ is hydrogen, $C_1$–$C_4$ alkyl, bromo, fluoro, chloro or iodo;

or a pharmaceutically-acceptable salt thereof for the manufacture of a medicament for immunosuppressive therapy of the human or animal body.

The present invention is further directed to the use of a compound of formula I for the manufacture of a medicament for treating auto-immune diseases in humans and animals.

The present invention also provides the use of a compound of formula I for the manufacture of a medicament for suppressing rejection of transplants in humans and animals, preferably for suppressing rejection of bone marrow transplants, cardiac transplants, cornea transplants, intestine transplants, liver transplants, lung transplants, pancreas transplants, renal transplants and skin transplants.

In another aspect of the invention the compound of formula I is used for the manufacture of a medicament for the treatment of a disease or condition selected from: acne rosacea, acrodermatitis continua, actinic reticuloid, AIDS, alopecia, Alport's syndrome, amyotrophic lateral sclerosis, aphthous stomatitis, red-cell aplasia, aplastic anemia, asthma, atopic dermatitis, autoimmune enteropathy, Behcet's syndrome, bullous erythema multiforme, bullous pemphigoid, biliary cirrhosis, corneal melting syndrome, Crohn's disease, dermatitis herpetiformis, dermatomyositis, diabetes mellitus, Duchenne muscular dystrophy, eczema, epidermolysis bullosa, erythema nodosum leprosum, familial hemophagocytic lymphohistiocytosis, Felty's syndrome, granuloma annulare, Grave's ophthalmopathy, hemolytic anemia, hemophilia, hepatitis, ichthyosis, inflammatory bowel disease, interstitial cystitis, interstitial lung disease, Keratoconjunctivitis, Langerhans cell histiocytosis, T-cell leukemias, B-cell leukemias, lymphomas, lichen planus, macrophage activation syndrome, Mooren's ulcer, morphea, multiple sclerosis, myasthenia gravis, nephropathy, nephrotic syndrome, palmo-plantar pustulosis, pemphigus, persistent photosensitivity, pityriasis rubra pilaris, polymyositis, psoriasis, psoriatic arthritis, pulmonary fibrosis, pyoderma gangrenosum, reticular erythematous mucinosis, rheumatoid arthritis, sarcoidosis, scleritis, scleroderna, serpiginous choroiditis, Sjogren's syndrome, sprue, Sweet's syndrome, systemic lupus erythematosus, systemic sclerosis, thrombocytopenia, toxic epidermal necrolysis, ulcerative colitis, uveitis, Weber-Christian disease, drug-induced Weber-Christian panniculitis, Wegener granulomatosis.

Preferably, 2'-deoxy-2',2'-difluorocytidine of the formula II

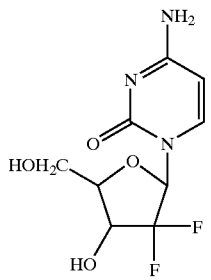

or a pharmaceutically-acceptable salt thereof is employed as the compound for above uses. Preferably, the pharmaceutically-acceptable salt employed is the hydrochloride.

The present invention is also directed to the use of gemcitabine hydrochloride in combination with one or more of cyclosporin A, tacrolimus, mycophenolate mofetil, daclizumab, rapamycin and one or more corticosteroid(s).

Pharmaceutical compositions in unit dose form comprising from 1 to 10 mg of gemcitabine hydrochloride and a pharmaceutically-acceptable carrier, diluent or excipient therefor are provided as another aspect of the invention.

The present invention further provides pharmaceutical compositions comprising a compound of formula I or a pharmaceutically-acceptable salt thereof; one or more of cyclosporin A, tacrolimus, mycophenolate mofetil, daclizumab, rapamycin and one or more corticosteroid(s); and a pharmaceutically-acceptable carrier, diluent or excipient therefor.

Pharmaceutical products containing a compound of formula I or a pharmaceutically-acceptable salt thereof and one or more of cyclosporin A, tacrolimus, mycophenolate mofetil, daclizumab, rapamycin and one or more corticosteroid(s) in combination for simultaneous, separate or sequential use for therapy of the human or animal body are provided as yet another aspect of the present invention.

Preferably, 2'-deoxy-2',2'-difluorocytidine of formula II or a pharmaceutically-acceptable salt thereof is employed as the compound for the pharmaceutical compositions and pharmaceutical products of the present invention. Preferably, the pharmaceutically-acceptable salt employed is the hydrochloride.

DETAILED DESCRIPTION OF THE INVENTION

Figure 1:
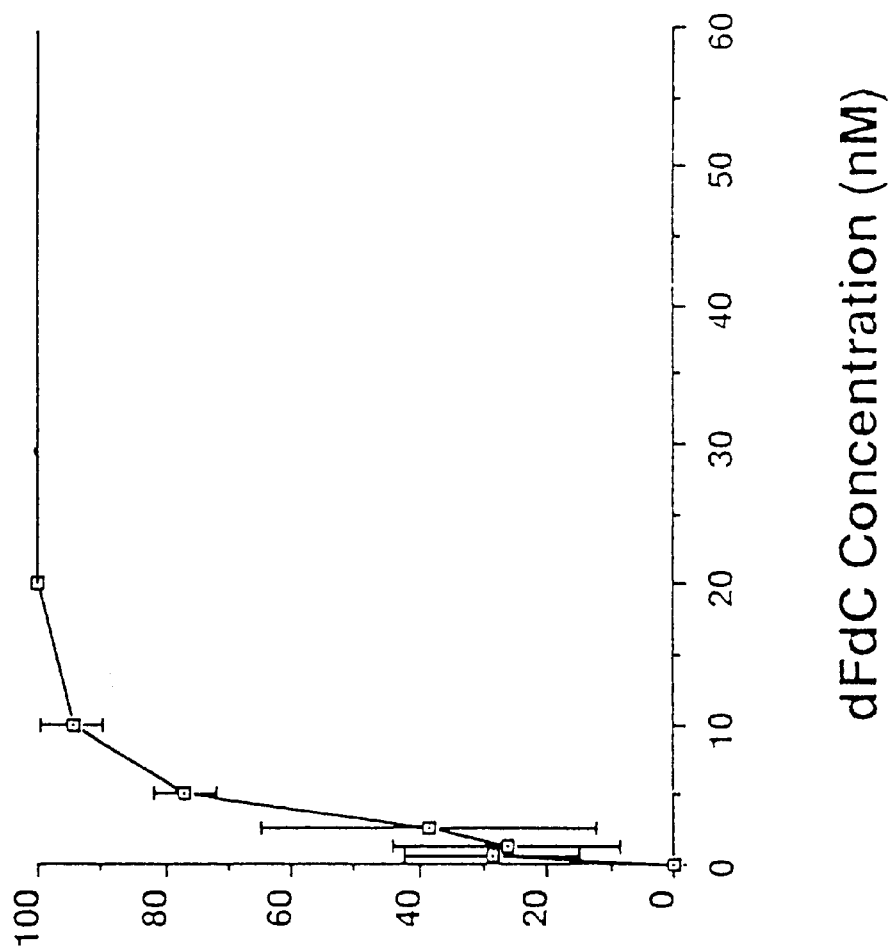
FIG. 1. PHA-induced lymphocyte proliferation is inhibited by dFdC in a dose-dependent manner with a 50% inhibition at a concentration of 3.25±0.9 nmol/l.

The compounds of formula I (2',2'-difluoronucleosides) employed in the present invention are preferably prepared by reacting a D-glyceraldehyde ketonide with a $C_1$–$C_4$ alkyl bromodifluoroacetate to afford an alkyl 3-dioxolanyl-2,2-difluoro-3-hydroxypropionate. The hydroxypropionate is hydrolyzed to a lactone which is protected and reduced to afford a 2-desoxy-2,2-difluororibose or xylose derivative. The hydroxy group of this compound is provided with a leaving group, and the resulting carbohydrate is coupled with an appropriate base. The resulting protected nucleoside is finally deprotected to provide a compound for use in the present invention. Details of a process such compounds for use in the present invention are described in U.S. Pat. No. 5,464,826 which is incorporated herein by reference.

Cyclosporin A, tacrolimus, mycophenolate mofetil, daclizumab, rapamycin and corticosteroids are commercially available.

The pharmaceutical compositions and products of the present invention are pharmaceutical formulations comprising the active ingredient (compound of formula I) and a pharmaceutical carrier, diluent or excipient therefor. The formulation of the compositions and products is conventional, and follows the usual practices of pharmaceutical chemists.

The active ingredient will be present in the formulation in the range of 1% to 90% by weight. The active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus the compositions and products can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions and products of the invention may be formulated so as to provide quick, sustained release of the ingredient after administration to the patient or animal by employing procedures well known in the art.

The compositions and products are preferably formulated in a unit dosage form, each dosage containing from about 0.1 to about 100 mg of the active ingredient. The term "unit dosage form" refers to physically discrete units suitable as unitary dosages for human subjects and other mammals, each unit containing a predetermined quantity of active ingredient calculated to produce the desired therapeutic effect, in association with a suitable pharmaceutical carrier.

If the active ingredient is gemcitabine hydrochloride the unit dosage preferably ranges from about 0.5 to about 25 mg and more preferably from about 1 to about 15 mg. It is particularly preferred that the unit dose of gemcitabine hydrochloride ranges from about 1 to about 10 mg and most preferably from about 2 to about 5 mg.

The following formulation examples represent specific pharmaceutical formulations partly employing gemcitabine hydrochloride as the active ingredient. The formulations may employ as active ingredients any of the compounds of formula I. The examples are illustrative only and are not intended to limit the scope of the invention in any way.

Formulation 1

Hard gelatin capsules are prepared using the following ingredients wherein "Active ingredient" is a compound of formula I:

|  | Quantity (mg/capsule) |
|---|---|
| Active ingredient | 25 |
| Starch dried | 425 |
| Magnesium stearate | 10 |

The above ingredients are mixed and filled into hard gelatin capsules in 460 mg quantities.
Formulation 2
A tablet formula is prepared using the ingredients below:

|  | Quantity (mg/tablet) |
|---|---|
| Active ingredient | 2 |
| Cellulose, microcrystalline | 500 |
| Silicon dioxide, fumed | 10 |
| Stearic acid | 8 |

The components are blended and compressed to form tablets each weighing 520 mg.
Formulation 3
An aerosol solution is prepared containing the following components:

|  | Weight % |
|---|---|
| Active ingredient | 0.10 |
| Ethanol | 29.90 |
| Propellant 22 (Chlorodifluoromethane) | 70.00 |

The active ingredient is mixed with ethanol and the mixture added to a portion of the propellant 22, cooled to −30° C. and transferred to a filling device. The required amount is then placed in a stainless steel container and diluted with the remainder of the propellant. The valve units are then fitted to the container.
Formulation 4
Tablets each containing 5 mg of active ingredient are made up as follows:

| Active ingredient | 5 mg |
|---|---|
| Starch | 75 mg |
| Microcrystalline cellulose | 58 mg |
| Polyvinylpyrrolidone (as 10% solution in water) | 5 mg |
| Sodium carboxymethyl starch | 5.5 mg |
| Magnesium stearate | 0.5 mg |
| Talc | 1 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.
Formulation 5
Capsules each containing 0.5 mg of active ingredient are made as follows:

| Active ingredient | 0.5 mg |
|---|---|
| Starch | 98.5 mg |
| Microcrystalline cellulose | 98.5 mg |
| Magnesium stearate | 2.5 mg |

The active ingredient, cellulose, starch and magnesium stearate are blended, passed through a No. 45 mesh U.S. sieve, and filled into hard gelatin capsules in 200 mg quantities.
Formulation 6
Suppositories each containing 0.1 mg of active ingredient are made as follows:

| Active ingredient | 0.1 mg |
|---|---|
| Saturated fatty acid glycerides to | 2 g |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.
Formulation 7
Suspensions each containing 10 mg of active ingredient per 5 ml dose are made as follows:

| Active ingredient | 10 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The active ingredient is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.
Intravenous formulations are prepared as follows:

| Formulation 8 | |
|---|---|
| Gemcitabine HCl | 0.1 mg |
| Isotonic saline | 1000 ml |
| Formulation 9 | |
| Gemcitabine HCl | 0.5 mg |
| Isotonic saline | 1000 ml |
| Formulation 10 | |
| Gemcitabine HCl | 10 mg |
| Isotonic saline | 1000 ml |
| Formulation 11 | |
| Gemcitabine HCl | 5 mg |
| Isotonic saline | 1000 ml |
| Formulation 12 | |
| Gemcitabine HCl | 10 mg |
| Isotonic saline | 1000 ml |

-continued

| Formulation 13 | |
|---|---|
| Gemcitabine HCl | 15 mg |
| Isotonic saline | 1000 ml |
| Formulation 14 | |
| Gemcitabine HCl | 25 mg |
| Isotonic saline | 1000 ml |

The solution of the above ingredients is administered intravenously at a rate of, for example, 1 ml/minute.

The compositions and products of the invention can be administered to the human or animal body by various routes including the oral, rectal, transdermal, subcutaneous, intravenous, intramuscular or intranasal routes. If gemcitabine hydrochloride is the active ingredient it is preferably administered via the IV route.

Dosages per day will normally fall within the range of about 0.01 to about 10 mg/kg of body weight (BW) in single or divided doses. Preferably dosages per day range from about 0.025 to about 5 mg/kg, and most preferably from about 0.05 to 0.25 mg/kg. However it will be understood that the amount of compound actually administered will be determined by a physician, in the light of the relevant circumstances including the condition to be treated, the particular compound to be administered, the chosen route of administration, the age, weight, and response of the individual patient, and the severity of the patient s symptoms, and therefore the above dosage ranges are not intended to limit the scope of the invention in any way.

The immunosuppressive effect of a representative compound of formula I, 2'-deoxy-2',2'-difluorocytidine (gemcitabine, dFdC), has been demonstrated by the in vitro and in vivo tests described below. The use of dFdC represents only a preferred embodiment of the invention and is not intended to be limiting in any respect to the scope of the invention and should not be so construed.

dFdC is a pyrimidine antimetabolite with antineoplastic activity against a wide range of solid tumors including metastatic pancreatic carcinoma, non-small cell lung cancer, ovarian and breast cancer. Kaye, *J. Clin. Oncol.* 12, 1527 (1994). It is a deoxycytidine analog which on entry into the cell is phosphorylated by deoxycytidine kinase in a stepwise fashion to the corresponding ultimate di- and triphosphate. Plunkett et al., *Nucleosides Nucleotides* 8, 775 (1989). Incorporation of the triphosphate of dFdC into DNA is assumed to be the main mechanism as it causes inhibition of DNA synthesis and cell death.

A number of phase I trials have been conducted with dFdC as anticancer drug, and most experience has been gained in phase II studies with the weekly schedule. Kaye, *J. Clin. Oncol.* 12, 1527 (1994). In this treatment regimen dFdC is given intravenously over 30 minutes once per week for 3 weeks followed by a week's rest. This type of administration is reported to induce myelosuppression with severe infections (WHO grade III/IV) in less than 1% of patients. Even after repeated applications of dFdC no significant reduction of CD4+ and CD8+ lymphocyte subsets, i.e. no significant immunosuppression, has been found. Dalkeler et al., *Anti-Cancer Drugs* 8, 643 (1997). In contrast, treatment of low malignant lymphomas with a purine analog like 2-chlorodeoxyadenosine (cladribine, 2-CdA) on the daily×5 schedule is associated with severe suppression of CD4+ lymphocytes for more than 12 months. Seymour et al., *Blood* 83, 2906 (1994).

Phase I studies testing dFdC on a daily×5 schedule at the 9 mg/m$^2$ dose level caused a significant amount of nonhaematologic toxicity including sporadic fever and severe hypertension. O'Rourke et al., *Eur. J. Cancer* 30A, 417 (1994). Because of these results this regimen was not recommended for further evaluation. Measurements of intracellular dFdC accumulation after daily application of low doses and its effect on immunocompetent cells have not been conducted previously.

For the purpose of the present invention the immunosuppressive effect of dFdC has been evaluated by testing the in vitro effect of dFdC on lymphocytes by using the lymphocyte colony-growth assay and by investigating the effect of dFdC in a rat heart-transplantation model.

Effects of dFdC on T-lymphocyte Colony Formation dFdC is commercially available. It is known that interference of drugs with the colony forming capacity of activated T-lymphocytes is an acceptable tool to demonstrate lymphocytotoxic effects. Aye, *Blood* 58, 1043 (1981). Therefore, peripheral blood mononuclear cells (PBMC) were cultured with phytohemagglutinin (PHA) and varying concentrations of dFdC in the microagar culture system described by Petzer et al., *Blood* 78, 2583 (1991). PBMCs were suspended in Iscove s medium containing 20% fetal calf serum and 0.3% agar. Subsequently 250 $\mu$l aliquots of this suspension containing 2×10$^5$ PBMCs were plated in multiwell tissue culture plates. The agar was allowed to solidify at room temperature and then was overlayered with 250 $\mu$l medium containing 0.5% PHA and 0.5% 2-mercaptoethanol (1×10$^{-4}$ mol/l final concentrations). The cultures were incubated at 37° C. in a fully humidified atmosphere containing 5% $CO_2$ and colonies were scored using an inverted microscope after 7 days of incubation.

As shown in FIG. 1, PHA-induced lymphocyte proliferation is inhibited by dFdC in a dose-dependent manner with a 50% inhibition at a concentration of 3.25±0.9 nmol/l.

Effects of dFdC in the Rat Heart-transplantation Model

Inbred male LEWIS (LEW) rats and Brown Norway (BN) rats weighing 200–270 g were obtained from "Zentralinstitut fur Versuchstierzucht", Hannover, Germany. Heterotopic heart transplants were performed using microsurgical techniques as described by Schmid et al., *Eur. Surg. Res.* 30, 61(1998). Postoperatively, all animals were given water and standard rat diet ad libitum.

dFdC was administered subcutaneously once daily for 50 consecutive days beginning immediately after surgery. The daily dosages (number of animals/group) were 25 (n6), 50 (n=5), 75 (n=6), 100 (n=6) 125 (n=6), 150 (n=6), 300 (n=6), 600 (n=2) or 6000 (nl) $\mu$g/kg body weight (BW). The control group (n=8) received no treatment.

The beating activity of heart allografts was determined by daily palpation. Animals were sacrificed by an overdose of ether whenever cardiac allografts stopped beating and hearts and all vital organs were excised for histology. Multiple sections of the left ventricle of the transplant and of every native organ were fixed in 4% buffered formalin. Paraffin-embedded probes were cut into 5-jim-thick sections and stained with hematoxylin and eosin. Slides were assessed by a pathologist blinded to the study and rejection was graded according to the ISHT criteria. Billingham et al., *J. Heart Transplant* 9, 587 (1990).

The effect of dFdC in the rat heart-transplantation model are shown in Table 1. The results are expressed as days of allograft survival for the different dFdC dose groups and the control group dFdC treatment.

Dose-dependent leucopenia occurred in all animals of all groups and was reversible in animals given less than 150 $\mu$g/kg of dFdC.

TABLE 1

| dFdC dose (μg/kg/day) | Allograft survival (days) | Graft rejection |
|---|---|---|
| Untreated controls | 7.1 | Grade IV |
| 25 | 7.3 | Grade IV |
| 50 | 9.2 | Grade IV |
| 75 | 15.7 | Grade IV |
| 100 | 152.8 | Grade IV |
| 125 | 144.2 | Grade IV |
| 150 | 41.5 | None |
| 300 | 16.0 | None |
| 600 | 10.5 | None |
| 6000 | 4.0 | None |

The results of above studies demonstrate for the first time a remarkable immunosuppressive potency of dFdC. Graft survival was prolonged in all animals given between 75 and 600 μg/kg BW of the drug as compared to untreated controls. Longest survival was achieved with 100 to 125 μg/kg BW. More than 125 μg/kg BW caused overimmunosuppression and irreversible myelotoxicity.

Surprisingly the effective immunosuppressive dose of dFdC as demonstrated by above results is much lower than would have been expected from the doses of the drug needed in the treatment of malignant disease.

What is claimed is:

1. A pharmaceutical composition comprising:
   (a) a compound of Formula I as follows:

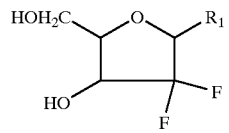

(I)

where:
$R^1$ is a base defined by one of the Formulae:

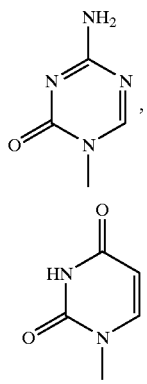

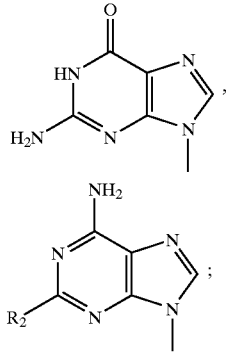

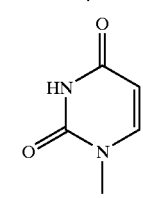

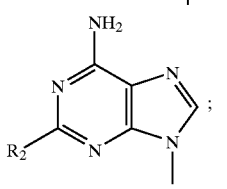

$R^2$ is hydrogen, $C_1$–$C_4$ alkyl, bromo, fluoro or iodo;
or a pharmaceutically acceptable salt thereof;

(b) one or more of the following: cyclosporin A, tacrolimus, mycophenolate mofetil, daclizumab, rapamycin and one of more corticosteroid(s); and
   (c) a pharmaceutically-acceptable carrier, diluent or excipient therefore.

2. A pharmaceutical composition according to claim 1 in which said compound of Formula I is 2',2'-deoxy-2'2'-difluorocytidine of Formula II

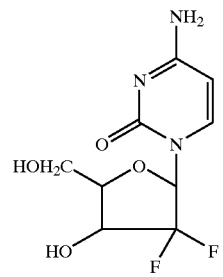

(II)

or a pharmaceutically-acceptable salt thereof.

3. A pharmaceutical composition according to claim 2 in which said pharmaceutically-acceptable salt is the hydrochloride.

4. The method of suppressing rejection of transplants in mammals comprising administering to said mammal a therapeutically effective amount of a compound of Formula I:

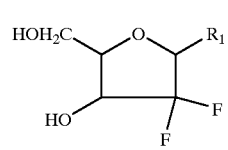

(I)

where:

$R^1$ is a base defined by one of the Formulae:

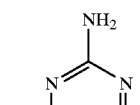

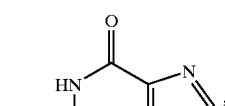

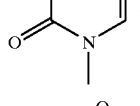

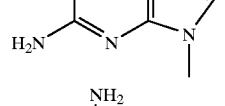

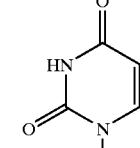

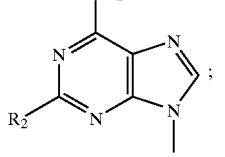

$R^2$ is hydrogen, $C_1$–$C_4$ alkyl, bromo, fluoro or iodo;

or a pharmaceutically acceptable salt thereof.

5. The method according to claim 4 of suppressing rejection of bone marrow transplants, cornea transplants, intestine transplants, liver transplants, lung transplants, pancreas transplants and skin transplants.

6. The method of claim 4 or 5 wherein said compound of Formula 1 is 2'-deoxy-2'2'-difluorocytidine of the Formula II:

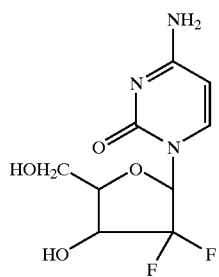

(II)

or a pharmaceutically acceptable salt thereof.

7. The method of claim 6 wherein the pharmaceutically acceptable salt thereof is gemcitabine hydrochloride.

8. The method of claim 7 wherein the gemcitabine hydrochloride salt of Formula II is used in combination with one or more of the following: cyclosporin A, tacrolimus, mycophenolate mofetil, daclizumab, rapamycin, or one or more corticosteroid(s).

9. The method of using a compound of Formula I in immunosuppressive therapy.

10. The method of claim 9 wherein the compound of Formula I is gemcitabine hydrochloride.

* * * * *